United States Patent
Gross et al.

(10) Patent No.: US 11,103,228 B2
(45) Date of Patent: Aug. 31, 2021

(54) TISSUE RETRACTORS

(71) Applicant: GLOBUS MEDICAL, INC., Audubon, PA (US)

(72) Inventors: Michael A. Gross, Collegeville, PA (US); Timothy Guenot, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 20 days.

(21) Appl. No.: 16/369,559

(22) Filed: Mar. 29, 2019

(65) Prior Publication Data

US 2020/0305855 A1 Oct. 1, 2020

(51) Int. Cl.
*A61B 17/02* (2006.01)
*A61B 17/00* (2006.01)

(52) U.S. Cl.
CPC .. *A61B 17/0218* (2013.01); *A61B 2017/0046* (2013.01); *A61B 2017/00477* (2013.01); *A61B 2017/00809* (2013.01)

(58) Field of Classification Search
CPC . A61B 17/02; A61B 17/0206; A61B 17/0218; A61B 2017/0225; A61B 17/025; A61B 2017/0287
See application file for complete search history.

(56) References Cited

U.S. PATENT DOCUMENTS

| | | | |
|---|---|---|---|
| 5,755,661 A | 5/1998 | Schwartzman | |
| 6,146,401 A | 11/2000 | Yoon et al. | |
| 7,766,823 B2 | 8/2010 | Moll et al. | |
| 9,254,065 B2 | 2/2016 | Floyd et al. | |
| 9,445,800 B2 | 9/2016 | Nguyen | |
| 9,918,708 B2 | 3/2018 | Livne et al. | |
| 2012/0130180 A1* | 5/2012 | Pell | A61B 17/025 600/206 |
| 2014/0257035 A1* | 9/2014 | Blain | A61B 17/0206 600/104 |

* cited by examiner

*Primary Examiner* — Eduardo C Robert
*Assistant Examiner* — Christina Negrellirodriguez

(57) ABSTRACT

A surgical retractor for retracting body tissue in a therapeutic procedure includes a blade having a body portion and a plurality of elongate elements extending from the body portion. The plurality of elongate elements is separated a distance from one another along a length of the body portion and form one or more gaps therebetween. The plurality of elongate elements is connected by one or more cross connectors transverse to the plurality of elongate elements. The retractor blade is configured to permit movement of a lung being retracted.

20 Claims, 5 Drawing Sheets

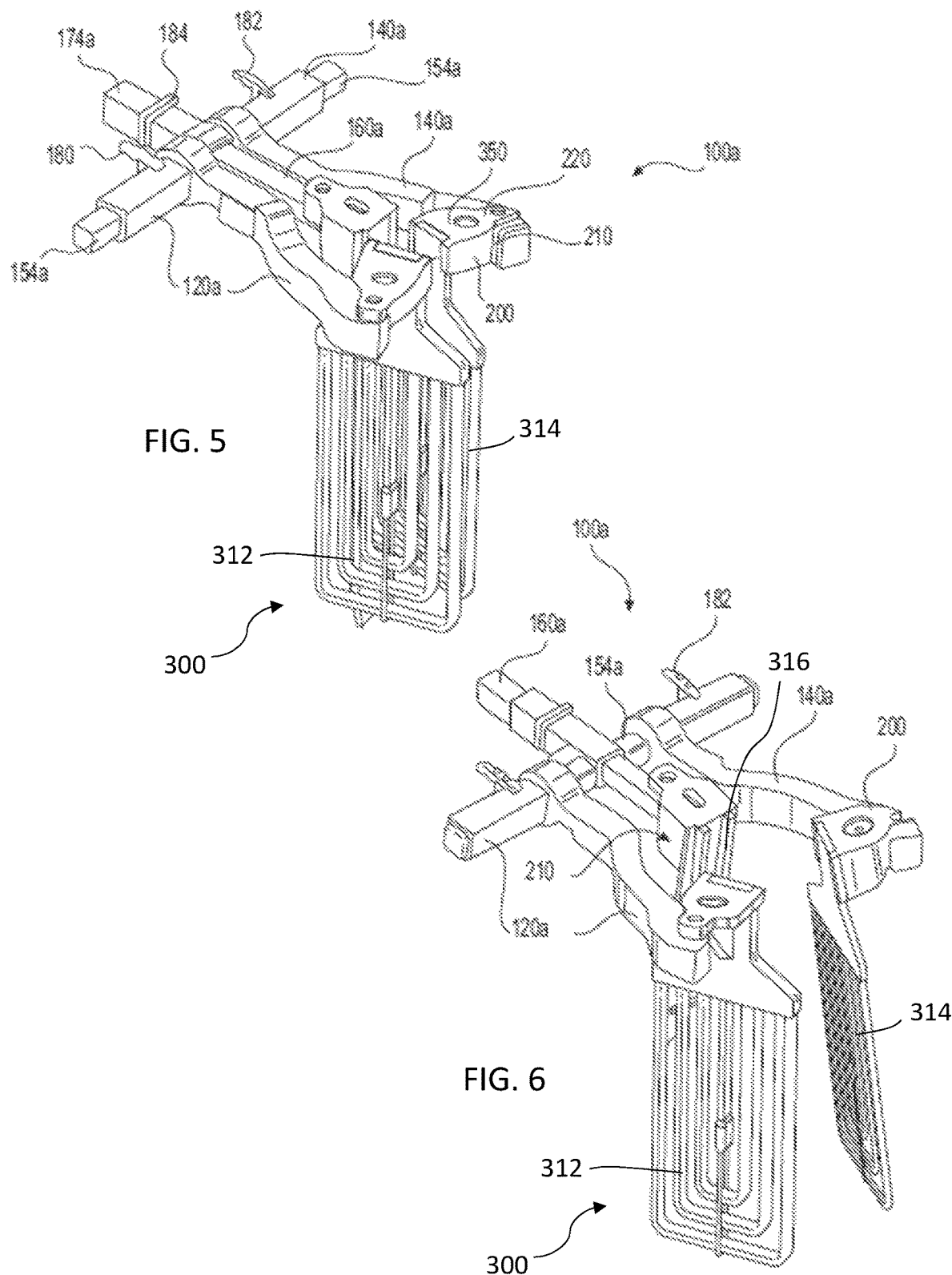

TISSUE RETRACTORS

FIELD

The invention relates to systems and methods for retracting body tissue during surgery, and more particularly to retractor blades.

BACKGROUND

Retractor systems may be used in a variety of different surgical procedures to provide an opening through which a doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site.

A retractor system may include one or more retractor blades. In use, the blades may be inserted into an incision and then retracted to displace tissue surrounding the incision along a path to the surgical site. To minimize trauma to the tissue, this tissue displacement may be generally refined and controlled.

SUMMARY

To meet this and other needs, retractor devices, systems, and methods are provided. The systems offer one or more surgical retractor blades for retracting body tissue. In an exemplary embodiment, the blade utilizes a flexible framework for lung retraction. In particular, a flexible metal wire geometry may be configured to permit movement of the lung. As the lung expands, the blade flexes, allowing movement, but not too much so as to allow the lung into the surgeon's field while operating. The retractor blade allows a user to retract a lung without inflicting damage on the lung or restricting patient breathing, for example.

In accordance with one embodiment, a surgical retractor for retracting body tissue in a therapeutic procedure comprises a retractor blade having a body portion and a plurality of elongate elements extending from the body portion, wherein the plurality of elongate elements is separated a distance from one another along a length of the body portion and form one or more gaps therebetween, wherein the plurality of elongate elements is connected by one or more cross connectors transverse to the plurality of elongate elements, and wherein the retractor blade is configured to permit movement of a lung being retracted.

In some embodiments, the retractor system or retractor blade may include one or more of the following features: the plurality of elongate elements is wires; the plurality of elongate elements is flexible such that they are able to flex when a force is applied, but rebound to its original position when the force is removed; the plurality of elongate elements is equally spaced along the length of body portion; the plurality of elongate elements is spaced and aligned such that they are substantially parallel to one another; the one or more cross connectors are positioned substantially perpendicular to the plurality of elongate elements; the plurality of elongate elements includes a center elongate element, and the center elongate element is aligned along a central longitudinal axis of the retractor blade; the plurality of elongate elements includes a first pair of elongate elements spaced apart and positioned laterally to the center elongate element, and the one or more cross connectors includes a first cross connector connecting the first pair of elongate elements; the plurality of elongate elements includes a second pair of elongate elements spaced apart and positioned laterally from the first pair of elongate elements, and the one or more cross connectors includes a second cross connector connecting the second pair of elongate elements; the plurality of elongate elements includes a third pair of elongate elements spaced apart and positioned laterally from the second pair of elongate elements, and the one or more cross connectors includes a third cross connector connecting the third pair of elongate elements; the first, second, and third cross connectors connect to the center elongate element; further comprising a frame portion comprising a fixed plate and a carriage, a first blade arm operably attached to the frame portion, a second blade arm operably attached to the frame portion, and a third blade arm operably attached to the frame portion, wherein the retractor blade and a second blade are attached to the carriage such that translation of the carriage causes the retractor blade and the second blade to translate; the frame portion comprises a first linear actuator for linearly translating the first arm and a second linear actuator for linearly translating the second arm; and/or further comprising a handle portion with a hand grip element, a neck, and an attachment portion, wherein the retractor blade is releasably coupled to the attachment portion with a pin.

In accordance with another embodiment, the surgical retractor system includes a retractor blade having a body portion and a plurality of elongate elements extending from the body portion, wherein the plurality of elongate elements is separated a distance from one another along a length of the body portion and form one or more gaps therebetween, wherein the plurality of elongate elements includes a center elongate element, a first pair of elongate elements spaced apart and positioned laterally to the center elongate element, a second pair of elongate elements spaced apart and positioned laterally from the first pair of elongate elements, and a third pair of elongate elements spaced apart and positioned laterally from the second pair of elongate elements, wherein a first cross connector connects the first pair of elongate elements, a second cross connector connects the second pair of elongate elements, and a third cross connector connects the third pair of elongate elements.

According to yet another embodiment, a method of retracting tissue may include inserting one or more retractor blades into a cavity and retracting soft tissue, such as lung tissue, wherein the tissue is able to enter the gaps between the elongate elements and the elongate elements are able to flex such that the retractor does not harm the tissue and/or cause problems to a breathing patient.

According to yet another embodiment, a kit includes one or more of the components, instruments, or systems described herein. For example, the kit may include a plurality of retractor blades, for example, of different sizes, shapes or configurations.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5 depicts a retractor according to another embodiment, including manually operable adjustment mechanisms for separating blades of the retractor with the blades in a closed configuration;

FIG. 6 depicts the retractor of FIG. 5 with the blades in an opened configuration;

DETAILED DESCRIPTION

Embodiments of the disclosure are generally directed to retractor blades, retractor systems, and methods of use. The retractor systems or devices may be suitable for retracting the lungs of a patient, which uses a flexible or semi-rigid device that accommodates for patient breathing. Although the retractor blades and systems exemplified herein are particularly suitable for lung retraction, it will be appreciated that the devices and systems may also be configured for retraction of other tissues or for other surgical procedures.

Figure 1:
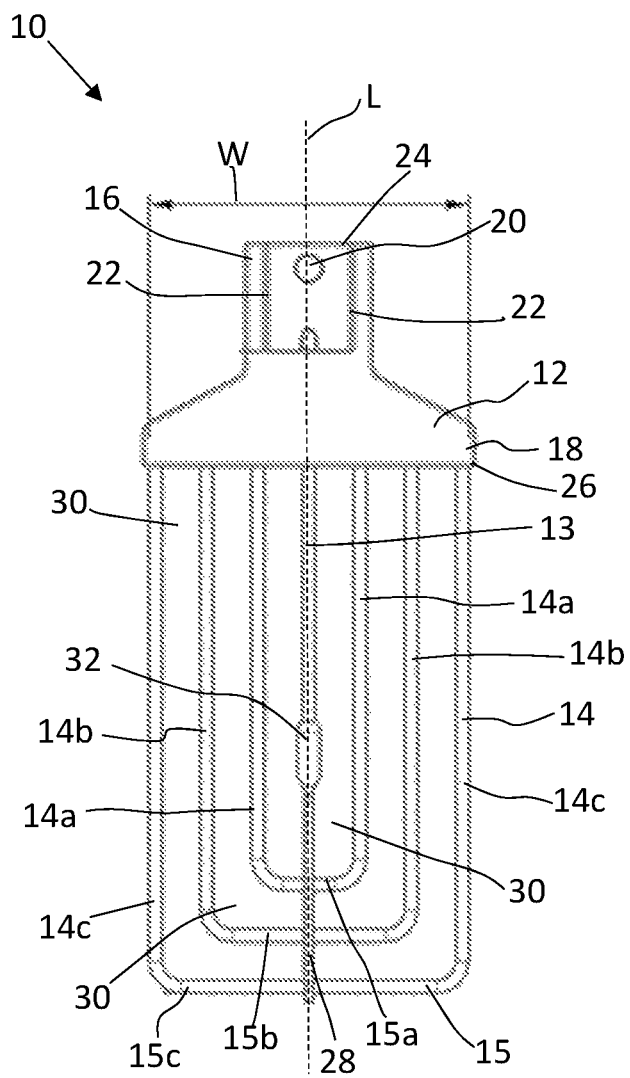
FIG. 1 depicts a retractor blade according to an exemplary embodiment.
Figure 2:
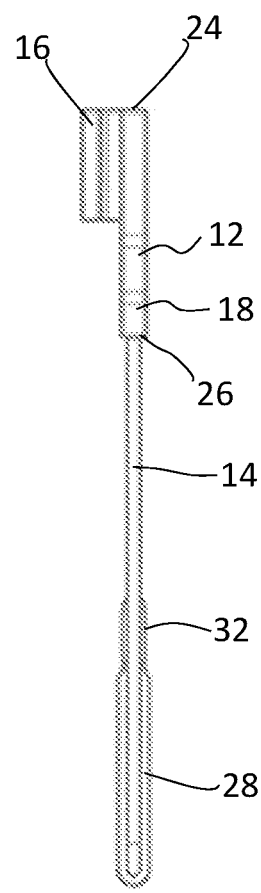
FIG. 2 depicts a side view of the retractor blade of FIG. 1.

FIGS. 1-2 illustrate a retractor blade 10 that may be suitable in retracting lung tissue, for example. The blade 10 may be comprised of a body portion 12 and a plurality of elongate elements 14. The body portion 12 may comprise a solid body extending from a proximal end 24 to a distal end 26 with a connector portion 16 toward the proximal end 24 and an extension portion 18 toward the distal end 26. The connector portion 16 may have one or more openings 20 or recesses 22 configured to mate with a retractor system. In particular, the connector portion 16 may be configured to interface with a handle of a hand-held retractor (FIGS. 9-11) or arms of a retractor (FIGS. 3-8) as described in more detail below. The extension portion 18 may have a width W greater than the connector portion 16. The extension portion 18 may be substantially flat with a thickness smaller than its width. As best seen in FIG. 2, the connector portion 16 may protrude rearwardly such that the thickness is greater at the proximal end 24 relative to the distal end 26 of the body portion 12.

The plurality of elongate elements 14 may extend from the distal-most end 26 of the extension portion 18. The elongate elements 14 may be in the form of elongated wire-shaped elements or wires. The wire-shaped elements 14 may be round, square, flat, or other suitable shape. The elongated wire-shaped elements 14 may be flexible or semi-rigid such that they are able to slightly flex, bend or curve when a force is applied, for example, against tissue, but rebound substantially to its original position when the force is removed. The wires may be comprised of metal, polymers, or any suitable biocompatible materials. Exemplary materials may include titanium (and titanium alloys), cobalt-chrome, stainless steel, aluminum, carbon fiber, and/or polyetheretherketone (PEEK), for example.

The plurality of elongate elements 14 may be separated a distance from one another along the length of the distal end 26 of the extension portion 18 to thereby form one or more gaps 30 therebetween. In particular, the plurality of elongate elements 14 may be equally spaced along the length of the extension portion 18, thereby resulting in equally sized gaps 30, although it will be appreciated that the number of elongate elements 14 and their position and spacing may be selected based on the dimensions of the blade 10 for a given type of patient and/or procedure. As best seen in FIG. 1, the plurality of elongate elements 14 may be spaced and aligned such that they are substantially parallel to one another. The elongate elements 14 may be connected via one or more cross connectors 15. The cross connectors 15 may be provided transverse to the elongate elements 14, for example, positioned substantially perpendicular to the elongate elements 14.

The plurality of elongate elements 14, for example, in the form of one or more wires, may be spaced apart and configured such that the entirety of elongate elements 14 and relative gaps 30 therebetween form a blade-like shape suitable for retracting movable tissues. In particular, the configuration of elongate elements 14 and associated spacing or gaps 30 allow for the overall blade 10 to retract soft tissues, such as lung tissue, allowing for some of the lung tissue to enter the gaps 30 between the elongate elements 14 and without harming the tissue. In addition, the wires 14 are able to gently flex to thereby provide sufficient but gentle retraction. Thus, the gentle retraction is less likely to cause problems to a breathing patient, for example, where the tissue is moving.

In the embodiment shown in FIG. 1, the plurality of elongate elements 14 include a center-most elongate element 13. The center-most elongate element 13 may be aligned along a central longitudinal axis L of the blade 300. A distal portion 28 of the center elongate element 13 may have a thickness greater than a thickness of the proximal portion of the center elongate element 13 and/or the general thicknesses of the other elongate elements 14. One or more of the elongate elements 14 may include an enlarged portion 32 having a surface area greater than the remainder of the elongate element 14.

A first pair of elongate elements 14a may be spaced apart and positioned laterally to the center elongate element 13. The first pair of elongate elements 14a, for example, at their distal ends, may connect via a first cross connector 15a. A second pair of elongate elements 14b may be spaced apart and positioned laterally from the first pair of elongate elements 14a. The second pair of elongate elements 14b may connect with a second cross connector 15b. A third pair of elongate elements 14c may be spaced apart and positioned laterally from the second pair of elongate elements 14b. The third pair of elongate elements 14c may connect via a third cross connector 15c.

One or more of the cross connectors 15 may connect to the center elongate element 13. For example, the first cross connector 15a may interface with the center elongate element 13 at a first position along the length of the center elongate element 13. The second cross connector 15b may interface with the center elongate element 13 at a second position along the length of the center elongate element 13. The third cross connector 15c may interface with the center elongate element 13 at a third position along the length of the center elongate element 13. The first position of the first cross connector 15a may be closest to the extension portion 18. The third position of the third cross connector 15c may be most distal and furthest from the extension portion 18. The second position of the second cross connector 15b may be located in between the first and third cross connectors 15a, 15c. The first, second, and third positions may be separated a distance from one another along the length of the center elongate element 13. In particular, the cross connectors 15 may be equally spaced toward the distal end of the center elongate element 13, although it will be appreciated that the cross connectors 15 may be appropriately spaced or positioned.

Figure 3:
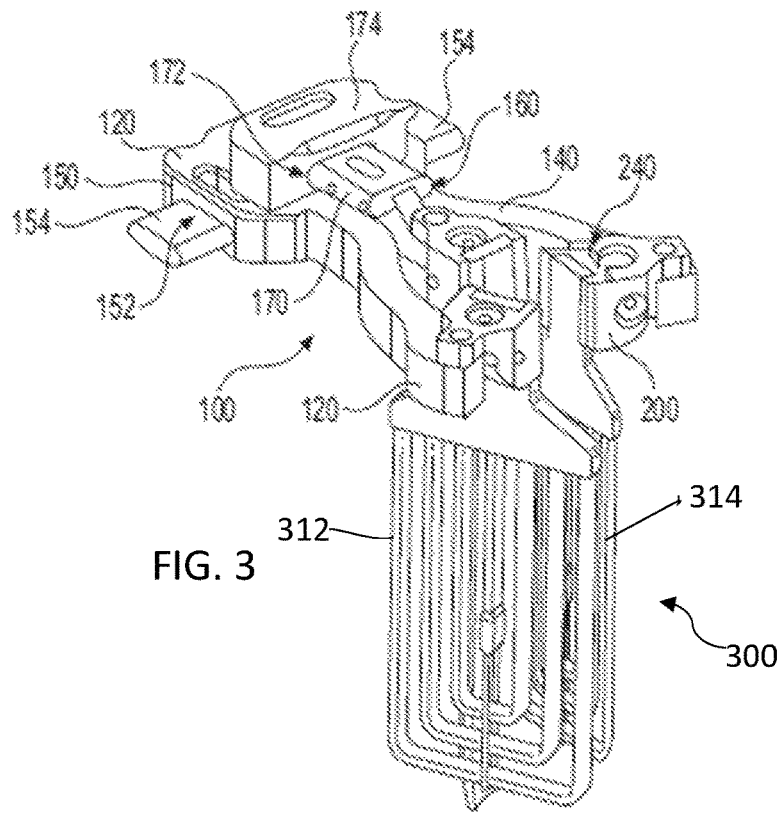
FIG. 3 depicts a surgical retractor blade system according to one embodiment.
Figure 4:
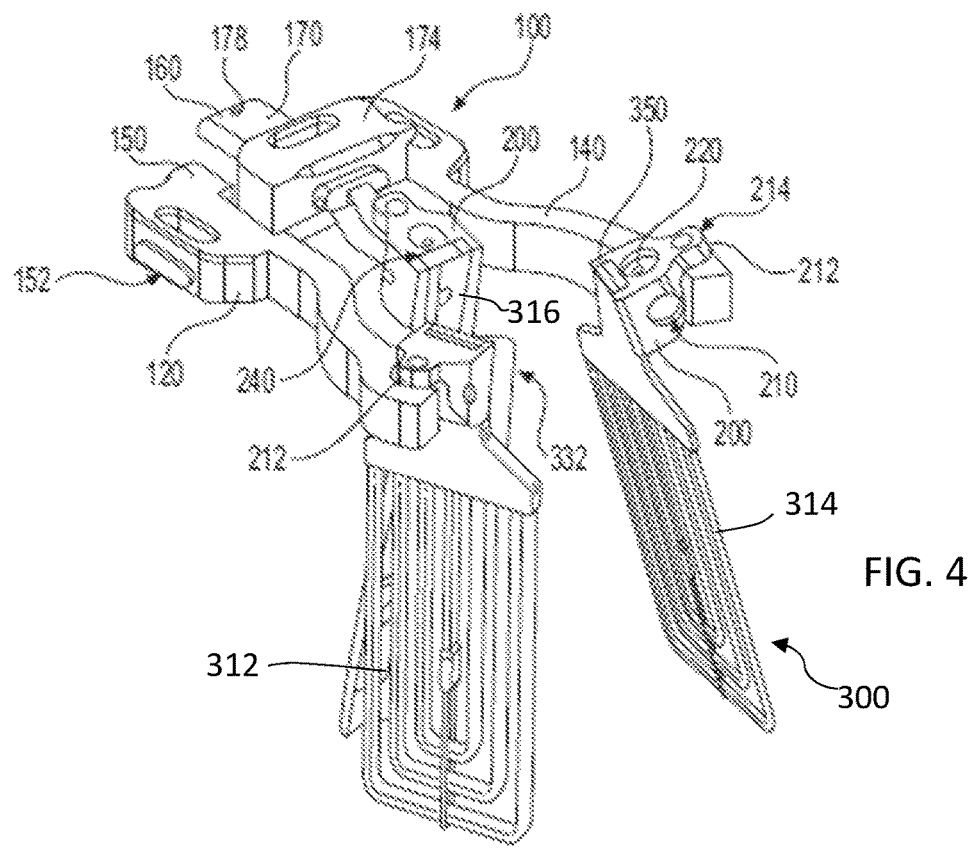
FIG. 4 depicts the retractor of FIG. 3, the blades relatively separated in a manner operative to retract tissue of the body in a therapeutic procedure.

FIGS. 3-4 illustrate a retractor system 100 that may be used to retract a patient's body tissue in a surgical procedure in accordance with one embodiment. Retractor system 100 includes a plurality of retractor blades 300, and in this embodiment, a first blade 312, a second blade 314, and a third blade 316 is shown. First and second blades 312, 314 are similar to blade 10 described in detail above. Accordingly, it will be appreciated that blades 312, 314 include like elements to blade 10. Blade 316 may comprise a solid blade. Although the blades 312, 314, 316 are shown in this configuration, it will be appreciated that different numbers and types of blades could be selected, substituted, or omitted depending on the surgical procedure.

Blades 300 are each coupled to the retractor frame 100, which includes first, second, and third arms 120, 140, and 160, each having a blade holder 200 for holding and positioning the blade 300. The blade holder 200 is configured to interface with the connector portion 16 of the blade 300. In one use of this embodiment, arms 120 and 140 are for cranial/caudal blades 312, 314, and arm 140 is for a posterior blade 316, although other orientations and uses are contemplated. In an embodiment, each blade 300 may be translated or indexed freely without a requirement to index another blade. In the embodiment shown, arms 120 and 140 are laterally located, and arm 160 is centrally located, although other relative dispositions are contemplated within the disclosure.

Retractor 100 may be configured to be adjusted into a desired position, and then releasably fixed to an operating table or other object in the operating theatre, so that a relative position of retractor 100 and a patient can be controlled. Fixation of one or more of retractor 100 can be accomplished using one or more of an operating room (OR) table clamp, a retractor table arm, an arm clamp, and a frame clamp, for example.

Arms 120, 140, and 160 are each linearly translatable to be moveable with respect to each other. More particularly, arms 120 and 140 each include a base 150 having a slot 152, sized to mateably receive and be linearly slideable upon an extension 154. In an embodiment, arms 120 and 140 are mirror images of each other, although this is not necessary in order to carry out all aspects of the disclosure. In the embodiment illustrated in FIGS. 3-4, extension 154 has a flattened profile, thereby preventing unintended rotation of arms 120, 140 with respect to each other, and as described below, with respect to arm 160. Other mechanical forms can be provided for extension 154, including for example a cylinder with a key, to enable a like purpose. In an alternative embodiment of the disclosure, any of arms 120, 140, and 160 can be rotated with respect to other of arms 120, 140, and 160, where extension 154 or 170 is non-keyed, for example cylindrical.

A threaded set screw (not shown), ratchet (shown in other embodiments herein), or other mechanism can be provided to retain arm 120, 140, 160 in a desired linearly translated position. A rack and pinion configuration can be provided, formed between extension 154 providing the rack, and with a pinion rotatably free but displaceably confined within arm 120, 140 and engaged with the rack. A locking mechanism, for example a set screw or a ratchet mechanism, can be provided to affix extension 154, 170 at a desired displacement.

Arm 160, in this embodiment, includes an arm extension 170 which translates within a slot 172 within a block 174, block 174 connected to extension 154, for example with screws, or by welding, adhesives, or any other known means. In this manner, an orientation of extension 154 maintains a desired or predetermined orientation with respect to slot 172. Accordingly, as arms 120, 140 are translated upon extension 154, or extension segments 154 that are mutually connected, and as arm 160 is translated within block 174, a relative path of arms 120, 140, and 160 is maintained. Further, each arm 120, 140, 160 is independently translatable with respect to the other arms. In this manner, a medical practitioner can retract tissue in a manner which best suits a therapeutic purpose. Arm extension 170 can be provided with an extension stop 178, to prevent an undesired separation of arm 160 from a remainder of retractor 100.

As can be seen in FIGS. 3-4, arms 120, 140 are sized and dimensioned to fit underneath block 174 when arms 120, 140 are approximated. In this manner, an overall dimension of retractor 100 is minimized, thereby reducing a physical obstruction introduced by retractor 100, and maximizing visualization within the surgical site. Arm 160 can be adjusted and affixed in any translated position as described with respect to arms 120, 160 upon extension 154, however a rack would be formed upon extension 170, and a pinion disposed within block 174.

It should be understood that in this embodiment, as well as other embodiments herein, while arms 120, 140 are configured to form a slot, and translate upon an extension, they could be configured to include extensions which translate within a block, as shown for arm 160. Similarly, arm 160 could form a block which slides upon an extension, as shown for arms 120, 140. In one aspect of the disclosure, the relative configuration of arms 120, 140 and arm 160 provides for an optimal packaging and a reduced physical profile, although various permutations of blocks and extensions as described herein can be provided, which can produce a reduced profile in a similar manner.

As can be seen in FIG. 3, blades 300 are aligned relative to each other. When retractor 100 is deployed, blades 300 can be inserted into an incision or opening in a patient's body, or can be positioned cooperative with one or more cannula, to progressively increase a size of an opening in a body sufficient to admit passage of retractor 100 with a minimum of disturbance to body tissue. As body tissue relaxes, or when desired, blades 300 can be separated or moved apart by moving arms 120 and 140 relatively apart. The relative extent of movement of arms 120, 140 do not have to be uniform, and at different times, enabling the medical practitioner to control a timing and extent of force exerted upon different portions of body tissue relative to each blade 312, 314. Similarly, blade 316, in connection with arm 160, can be moved before, during, or after movement of either of arms 120, 140, to be closer or further from blades 312, 314.

As blades 312, 314, and 316 are moved relatively apart, a perimeter defined by an exterior surface of blades 312, 314, and 316 is increased, moving body tissue apart, and increasing access to an area within the body. A greater or fewer number of arms 120, 140, and 160 can be provided upon retractor 100 in a like configuration as arms 120, 140, or 160, each configured to move independently of all other arms.

As can be seen in FIG. 4, blades 312, 314, and 316 can be pivoted to be angled or pitched with respect to their respective arms 120, 140, 160. In this manner, distal ends 330 of blades 300 can be further separated, and the perimeter defined by the exterior surface of the blades can be enlarged, without a necessity of increasing an overall profile of retractor 100, or moving arms 120, 140, 160 any further apart.

FIG. 3 depicts retractor 100 in a "closed" or non-retracted configuration, in accordance with one embodiment. In the closed configuration, blades 312, 314, and 316 are radially disposed around a central area 324. FIG. 4 depicts retractor system 100 in an "open" or retracted configuration, in which blades 312, 314, 316 have been pitched by being pivoted about a pivot 210 connected to a proximal end 332 of a blade 300, and to an arm 120, 140, or 160.

Blades 300 can each be independently pitched or translated, and can be independently pitched or translated with respect to other blades. A stop element 212, in the embodiment shown, a flange, extends from blade holder 200 and contacts arm 120, 140, or 160 at a desired extreme range of pivoting motion of blade holder 200 and associated blade 300. A screw (not shown) can be provided within aperture 214, which may be threaded, the screw configured to bear upon arm 120, 140, or 160 to cause pivoting of blade holder 200, or to function as a stop element operative to change a maximum range of pivoting motion.

Blade holder 200 is provided with a blade engagement profile 240 extending between opposing ends of blade holder 200. The connector portion 16 of the blade 300 is configured to be mateable with blade engagement profile 240, whereby when mated, blade 300 can be retained upon blade holder 200 and be slideable so that a penetration of blade 300 with respect to a patient is adjustable. Further, blades 300 can be replaced with blades having a different shape, size, or tissue engaging profile. In one embodiment, connector portion 16 and blade engagement profile 240 form a pin/recess, threaded connection, friction fit, dovetail connection, or other suitable engagement.

Additionally, blades 300 can be inserted after retractor 100 is fixed in a position with respect to a patient, whereby a blade can be slid upwards and away from the patient, and replaced, without a requirement to move retractor 100 or the patient. Blades 300 are affixed at a desired displacement along the length of connector portion 16 by a friction fit between connector portion 16 and blade engagement profile 240, or by a set screw or other fastener connected to blade holder 200 and contactable with blade 300 or connector portion 16.

In one embodiment, retractor 100 is configured for an anterior approach to the spine of the patient. In this embodiment, shown in FIGS. 3-4, arms 120, 140 support caudal oriented blades, and arm 160 supports a cranial oriented blade. A range of pitch motion for blades 300 can include 0 degrees to 20 degrees, although substantially larger angulation can be provided, for example 30, 40, or 50 degrees, or a greater range of angulation.

In surgical procedures where imaging is to take place, for example X-ray imaging, it is advantageous if at least blades 300 of retractor 100 are at least partially radiolucent, to foster visualization of the imaged area. Accordingly, blades 300 can be fabricated using aluminum, carbon fiber, or polymeric materials, or any other sufficiently strong and radiolucent material, or combination of materials, which is known or hereinafter developed.

With reference to FIGS. 5-8, in an alternative frame embodiment 100A, retractor 100A includes elements similar to those of the embodiment of FIGS. 3-4, and bears similar reference numbers. In FIGS. 5-6, arms 120A, 140A, and 160A support blades 300 in a manner similar to arms 120, 140, and 160 of FIGS. 1-2, but arms 120A, 140A form square or rectangular channels which translate upon extensions 154A. Similarly, arm 160A translates within a rectangular channel forming block 174A. Keys 180, 182, and 184 are positioned to be rotated by a medical practitioner while retractor 100A is deployed, thereby translating arm 120A, 140A, or 160A. With additional reference to FIGS. 7-8 and 11, each of keys 180, 182, and 184 are connected to a pinion rotatably fixed to arm 120A, 140A for keys 180, 182, and to block 174A for key 184. A toothed rack 186 is formed upon a side surface of each extension 154A, and a similar toothed rack 188 is formed upon a side surface of arm 160. In this manner, rotation of key 180, 182, or 184 causes a corresponding translational movement of arm 120A, 140A, and 160A, respectively. In FIG. 6, keys 180 and 182 have been rotated to separate arms 120A, 140A, and key 184 has been rotated to retract arm 160A.

Figure 7:
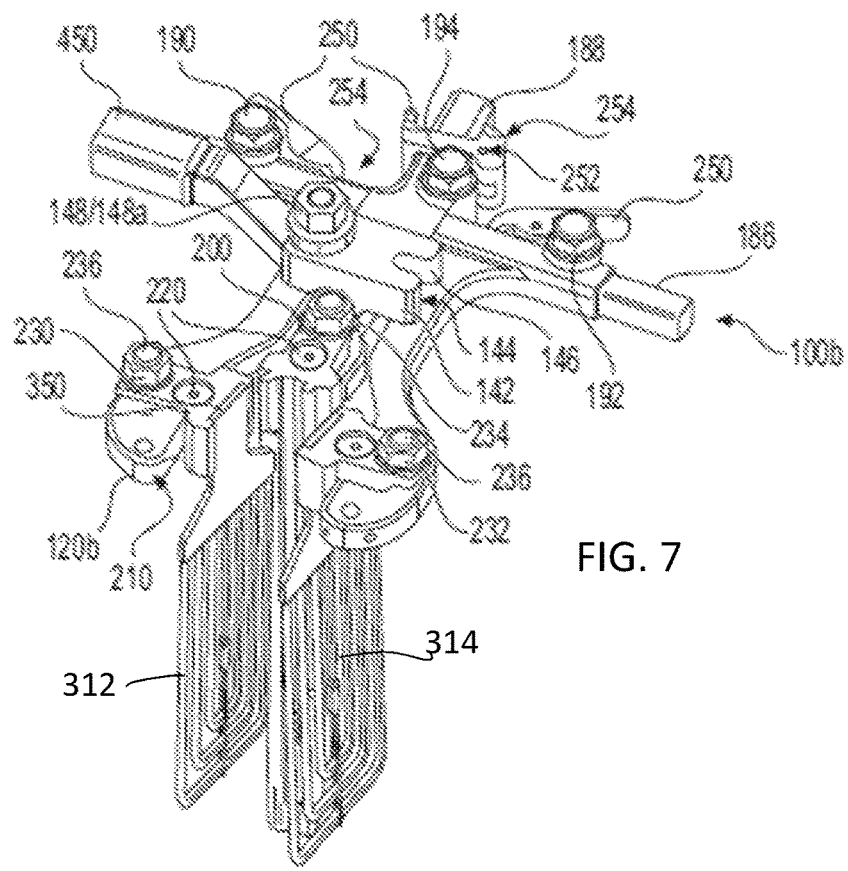
FIG. 7 depicts an alternative retractor according to another embodiment, including adjustment mechanisms operable with a tool with the blades in a closed configuration.
Figure 8:
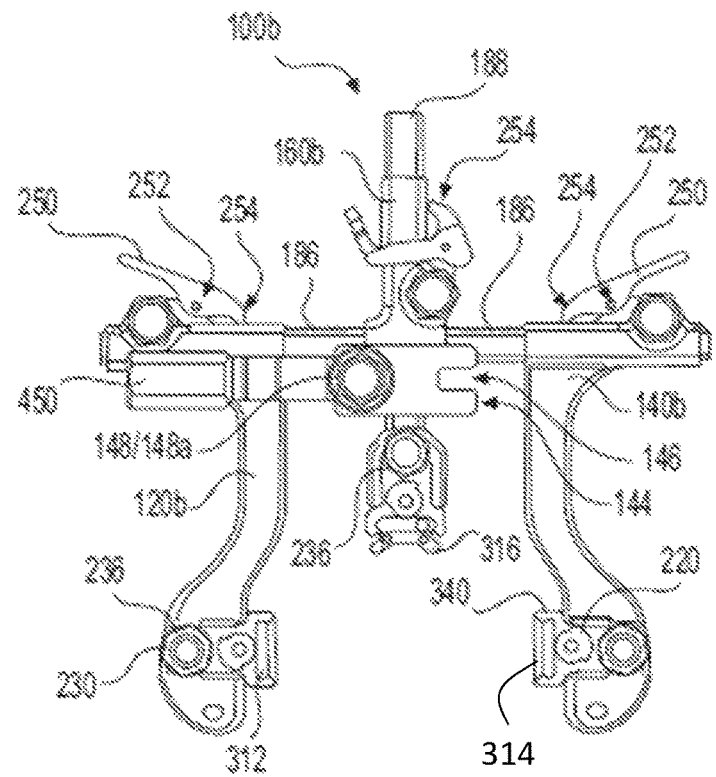
FIG. 8 depicts the retractor of FIG. 7 with the blades in an opened configuration.

In FIGS. 7-8, as can be seen in frame embodiment 100B, in place of keys 180, 182, and 184, tool engagements 190, 192, 194 are connected to rotatably fixed pinions mateable with racks 186, 188. Tool engagements 190, 192, and 194 are engageable by a driving tool, such as a hex or allen head driver. Accordingly, a driving tool (not shown) can be rotated by a hand of a medical practitioner, or by an electrical or computer controlled actuator, to adjust a position of arms 120B, 140B, or 160B, and thereby change a position of one or more blades 300, including for example blades 312, 314, or 316. It should be understood that either a key 180 configuration, or a tool engagement 190 configuration, as shown in FIGS. 5-8, can be provided in the embodiment of FIGS. 3-4.

With further reference to FIGS. 7-8, a blade pitch tool engagement 230, 232, 234 is provided, rotatable using a tool as described with respect to tool engagements 190, 192, and 194, and operative thereby to change a pitch of a blade 300 attached to blade holder 200.

More particularly, in one configuration, blade holder 200 is pivotally mounted at pivot 210, and blade pitch tool engagement 230, 232, and 234 are each rotatably retained upon their respective blade holder 200. Threaded shaft 236 is keyed to prevent rotation, but is axially displaceable by rotation of blade pitch tool engagement 230, 232, 234. As a result, shaft 236 can be caused to bear against arm 120B, 140B, 160B to cause rotation of blade holder 200 about pivot 210, and to thereby change an angle of blade 300. In another embodiment, blade pitch tool engagement 230, 232, 234 is affixed to shaft 236, and shaft 236 is threadably received within blade holder 200. Thus, as blade pitch tool engagement 230, 232, 234 is rotated, shaft 236 bears against its respective arm 120B, 140B, 160B. In a variation of this embodiment, shaft 236 is threadably received within arm 120B, 140B, 160B. Other variations, including a threaded blade holder 200, can be provided. In any of the foregoing embodiments, a biasing element (not shown) can be provided to bias blade holder 200 in a closed or pitched position, where a position of blade holder 200 is not positive controlled in each direction of rotation about pivot 210. It should be noted that in one embodiment, the blade holder 200 may be positively controlled in each direction about the pivot 210. While not shown for all embodiments, it should be understood that the foregoing blade holder pitch mechanism described for FIGS. 3-6 can be provided for other embodiments herein.

With further reference to FIGS. 7-8, a ratcheting pawl 250 can be provided, pivotable about pawl pivot 252, a pawl 250 provided for any or all actuators having a toothed rack, including arms 120B, 140B, and 160B, and all other embodiments herein upon which a rack is formed. A pawl tooth 254 has a sloped surface configured to allow rack 186, 188 to pass in one direction, but not an opposite direction. In the embodiment shown, pawl 250 enables arms 120B, 140B, and 160B to move apart, relative to each other. This operates to maintain tissue retracted during a therapeutic procedure. When the procedure is complete, or it is desired to otherwise remove retractor 100, pawl 250 can be rotated about pivot 252 to disengage pawl tooth 254 from rack 186, 188, whereupon key 180, 182, and 184, or tool engagement 190, 192, or 194 can be rotated to change a position of its associated arm.

In an alternative embodiment, pawl 250 does not include a sloped surface at pawl tooth 254, and accordingly the pawl must be retracted from contact with rack 186 or 188 to enable movement of the associated arm.

FIGS. 7-8 further illustrate a frame mount 142, which enables frame 100 (or frame 100A, 100B) of retractor 100 to be mounted to a table or other supporting structure with a single mounting point. A support coupling 450 is affixed to the supporting structure with a rod (not shown) threadably or otherwise securable within an end of coupling 450. Coupling 450 includes a threaded rod 148 and nut 148A extending from an end portion. Coupling 450 is inserted into chamber 144 of frame mount 142, and the attached threaded rod is passed into notch 146. Nut 148A is tightened to secure coupling 450 to frame mount 142, and thereby securing retractor 100 to a supporting structure. The frame mount 142 illustrated includes two notches 146, thereby enabling a support coupling to be connected to either side, or to both sides, of frame mount 142.

With further reference to FIGS. 7-8, a cam latch 220 is rotatably retained upon blade holder 200, and is oriented to engage a slot (not shown) within blade 300. In this manner, blade 300 is releaseably retained upon blade holder 200, and is prevented from sliding. Alternatively, cam latch 220 can overlap a protrusion (not shown) formed upon blade 300.

Figure 9:
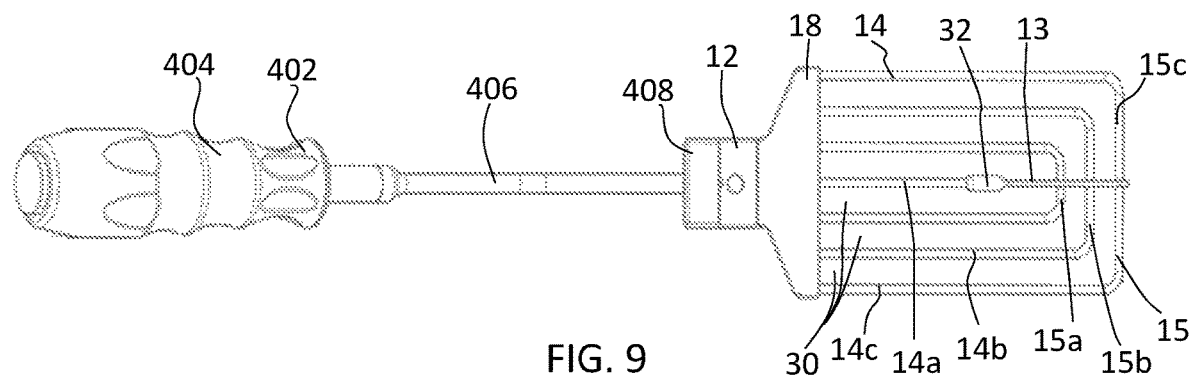
FIG. 9 depicts an alternative hand-held retractor according to another embodiment.
Figure 10:
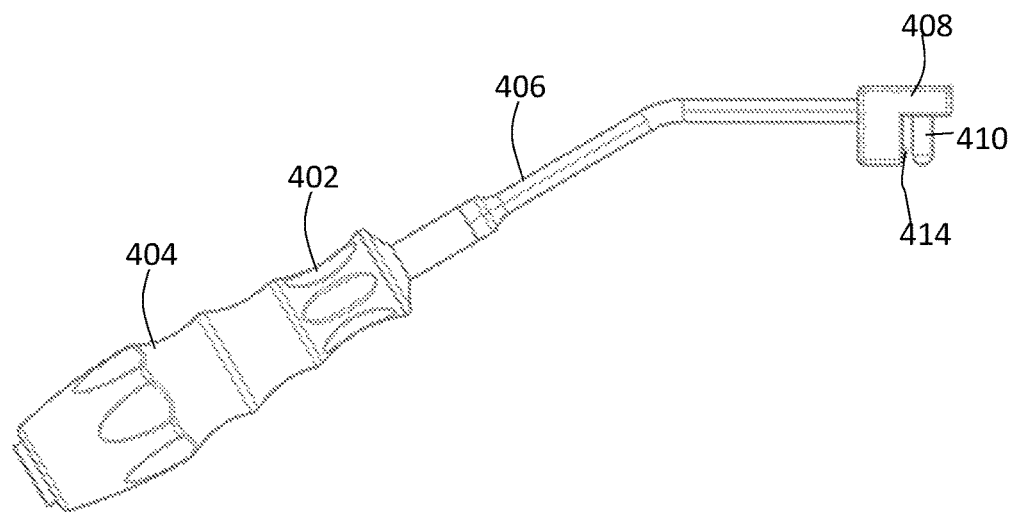
FIG. 10 shows a side view of the handle for the hand-held retractor of FIG. 9.
Figure 11:
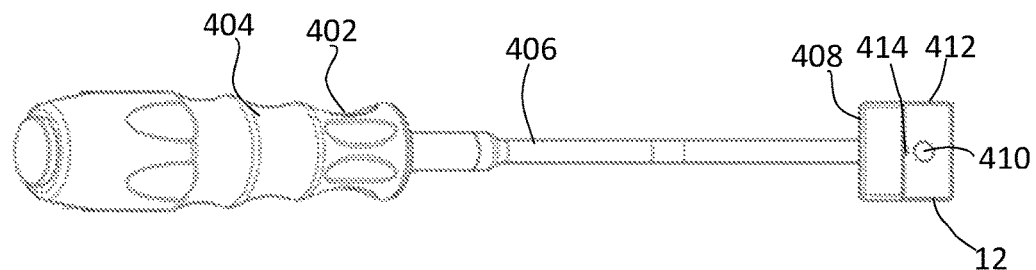
FIG. 11 depicts a bottom view of the handle for the hand-held retractor of FIG. 9.

Turning now to FIGS. 9-11, an alternative hand-held retractor 400 is shown. The hand-held retractor 400 may be configured to engage with the blade 10 described above. The hand-held retractor 400 may include a handle portion 402 with a hand grip element 404, a neck 406, and an attachment portion 408. The neck 406 may be straight or angled, as shown in FIG. 10. The attachment portion 408 may comprise a pin 410, which may be received in the opening 30 within the connector portion 16 of the blade 10. The pin 410 may be rotatable, threadedly connected, press-fit, or otherwise configured to removably couple blade 10 to handle portion 402 of retractor 400. The attachment portion 408 may also include one or more sides or tracks 412 configured to be received in corresponding recesses 22 of the connector portion 16. In addition, the attachment portion 408 may include one or more 414 protrusions, for example, aligned with the pin 410 to provide for an interference fit or friction fit between the attachment portion 408 of the retractor 400 and the connector portion 16 of the blade 10. It will be appreciated that one or more hand-held retractors 400 may be used alone, as a pair, or in combination with other retractor instruments when retracting tissue in a patient.

Various configurations of the retractor are contemplated and are not limited by the embodiments described with reference to the figures. For example, various sizes, shapes and types of retractors and blades are contemplated, and various materials can be used to construct the various parts. Material selected can be radiolucent or radiopaque, as desired. The exemplary embodiments provide various advantages, such as allowing users to retract a lung without inflicting damage on the lung or restricting patient breathing.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A surgical retractor system configured to permit movement of a lung comprising:
    a retractor blade having a body portion and a plurality of elongate elements extending from the body portion, wherein the plurality of elongate elements each have a proximal end and a distal end, wherein the plurality of elongate elements are separated a distance from one another along a length of the body portion and form one or more gaps therebetween, wherein the plurality of elongate elements are connected by one or more cross connectors transverse to the plurality of elongate elements,
    wherein the proximal ends of the plurality of elongate elements are connected to the body portion, and
    wherein the distal ends of the plurality of elongate elements are connected to one of the one or more cross connectors.

2. The surgical retractor system of claim 1, wherein the body portion includes a connector portion and an extension portion.

3. The surgical retractor system of claim 1, wherein the plurality of elongate elements are wires.

4. The surgical retractor system of claim 1, wherein the plurality of elongate elements is flexible such that they are able to flex when a force is applied, but rebound to its original position when the force is removed.

5. The surgical retractor system of claim 1, wherein the plurality of elongate elements is equally spaced along the length of body portion.

6. The surgical retractor system of claim 1, wherein the plurality of elongate elements is spaced and aligned such that they are substantially parallel to one another.

7. The surgical retractor system of claim 1, wherein the one or more cross connectors are positioned substantially perpendicular to the plurality of elongate elements.

8. The surgical retractor system of claim 1, wherein the plurality of elongate elements includes a center elongate element, and the center elongate element is aligned along a central longitudinal axis of the retractor blade.

9. The surgical retractor system of claim 8, wherein the plurality of elongate elements includes a first pair of elongate elements spaced apart and positioned laterally to the center elongate element, and the one or more cross connectors includes a first cross connector connecting the first pair of elongate elements.

10. The surgical retractor system of claim 9, wherein the plurality of elongate elements includes a second pair of elongate elements spaced apart and positioned laterally from the first pair of elongate elements, and the one or more cross connectors includes a second cross connector connecting the second pair of elongate elements.

11. The surgical retractor system of claim 10, wherein the plurality of elongate elements includes a third pair of elongate elements spaced apart and positioned laterally from the second pair of elongate elements, and the one or more cross connectors includes a third cross connector connecting the third pair of elongate elements.

12. The surgical retractor system of claim 11, the first, second, and third cross connectors connect to the center elongate element.

13. The surgical retractor system of claim 1 further comprising a frame portion comprising a fixed plate and a carriage, a first blade arm operably attached to the frame portion, a second blade arm operably attached to the frame portion, and a third blade arm operably attached to the frame portion, wherein the retractor blade and a second blade are attached to the carriage such that translation of the carriage causes the retractor blade and the second blade to translate.

14. The surgical retractor system of claim 13, wherein the frame portion comprises a first linear actuator for linearly translating the first arm and a second linear actuator for linearly translating the second arm.

15. The surgical retractor system of claim 1 further comprising a handle portion with a hand grip element, a neck, and an attachment portion, wherein the retractor blade is releasably coupled to the attachment portion with a pin.

16. A surgical retractor system comprising:
a retractor blade having a body portion and a plurality of elongate elements extending from the body portion, wherein the plurality of elongate elements is separated a distance from one another along a length of the body portion and forming one or more gaps therebetween,
wherein the plurality of elongate elements includes a center elongate element, a first pair of elongate elements spaced apart and positioned laterally to the center elongate element, a second pair of elongate elements spaced apart and positioned laterally from the first pair of elongate elements, and a third pair of elongate elements spaced apart and positioned laterally from the second pair of elongate elements,
wherein a first cross connector connects the first pair of elongate elements, a second cross connector connects the second pair of elongate elements, and a third cross connector connects the third pair of elongate elements,
wherein the first cross connector, second cross connector and third cross connector are spaced apart from each other.

17. The surgical retractor system of claim 16, wherein the plurality of elongate elements are wires.

18. The surgical retractor system of claim 16, wherein the plurality of elongate elements is flexible such that they are able to flex when a force is applied, but rebound to its original position when the force is removed.

19. The surgical retractor system of claim 16, wherein the plurality of elongate elements is spaced and aligned such that they are substantially parallel to one another.

20. The surgical retractor system of claim 16, wherein the first, second, and third cross connectors are positioned substantially perpendicular to the plurality of elongate elements.

* * * * *